United States Patent [19]

Jessel, Jr. et al.

[11] Plant 4,668

[45] Mar. 10, 1981

[54] CARNATION PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 89,729

[22] Filed: Oct. 31, 1979

[51] Int. Cl.[3] ..... A01H 5/00

[52] U.S. Cl. ..... Plt./71

[58] Field of Search ..... Plt./71

*Primary Examiner*—Robert E. Bagwill

*Attorney, Agent, or Firm*—Schwartz, Jeffery, Schwaab, Mack, Blumenthal & Koch

[57] ABSTRACT

A carnation plant known by the cultivar name Queen and particularly characterized as to uniqueness by the combined characteristics of commercial double flower type; flat flower form, twisting slightly with maturity; medium flower size; light salmon pink flower color with minimum color oxidization; medium flowering response; 4 to 7 flowers and buds showing color per flowering stem; medium peduncle length; strong peduncle strength; and tall plant height.

1 Drawing Figure

1

The present invention comprises a new and distinct cultivar of *Dianthus caryophyllus*, L., hereinafter referred to by the name Queen.

Queen is the product of a planned breeding program which had the objective of creating new spray type carnation cultivars in a wide color range with fast flowering response, unrestricted breaking action, vigorous growth, strong non-brittle stems, high bud and flower count, and attractive, durable flowers for year-round commercial production.

Queen was originated from a cross made in Barberton, Ohio in the year 1974. The male parent was a light pink unnamed seedling (#68026001). The female parent was a dark pink unnamed seedling (#72006011). Both parents are unpatented and were originated from the breeding program of the present inventors. Queen was discovered and selected as one flowering plant within a progeny of the stated parentage by Walter H. Jessel, Jr. and William E. Duffett on July 18, 1975 in a controlled environment in Barberton, Ohio.

The first act of asexual reproduction of Queen was accomplished when vegetative cuttings were taken from the initial selection in October, 1975 in a controlled environment in Barberton, Ohio by a technician working under formulations established and supervised by Walter H. Jessel, Jr. and William E. Duffett. Horticultural examination of selected units initiated June 13, 1977 has demonstrated that the combination of characteristics as herein disclosed for Queen are firmly fixed and are retained through successive generations of asexual reproduction.

Queen has not been observed under all possible environmental conditions. The phenotype may vary significantly with variations in environment such as temperature, light intensity, and daylength. The following observations, measurements, and comparisons describe plants grown in Barberton, Ohio and in Salinas, Calif. under greenhouse conditions which approximate those generally used in commercial practice.

The following traits have been repeatedly observed and are determined to be basic characteristics of Queen which in combination distinguish this carnation as a new and distinct cultivar:

(1) Commercial double flower type.

(2) Flat flower form, twisting slightly with maturity.

2

(3) Medium flower size, ranging from 45 to 60 mm in diameter.

(4) Light salmon pink flower color with minimum color oxidation.

(5) Medium flowering response.

(6) 4 to 7 flowers and buds showing color per flowering stem.

(7) Medium peduncle length, ranging from 10 to 12 cm.

(8) Strong peduncle strength.

(9) Tall plant height.

Of the several commercially available carnations known to the present inventors, the most similar in comparison to Queen are Sweetheart and Silvery Pink. Reference is made to Chart A which compares selected characteristics of Queen with those same characteristics of Sweetheart and Silvery Pink. General comparisons are as follows:

(1) In comparison to Sweetheart, Queen has smaller flower size, a greater number of buds and flowers per stem, shorter flowering response period, longer peduncle length, greater peduncle strength, and taller plant height. The flower color of Sweetheart is similar to that of Queen.

(2) In comparison to Silvery Pink, Queen has different flower color, smaller flower size, shorter flowering response period, shorter peduncle length, and taller plant height. The number of buds and flowers per stem of Queen is similar to that same characteristic of Silvery Pink.

The accompanying photographic drawing is a color photograph showing typical inflorescence and foliage characteristics of Queen. Colors are as nearly true as possible with illustrations of this type.

In the following description, color references are made to The Limit Color Cascade, by the Munsell Company, 1972 edition. Color values determined between 4:30 P.M. and 5:00 P.M. on June 13, 1977 under 150 foot-candle light intensity at Barberton, Ohio are denoted by (a). Color values determined between 8:00 A.M. and 8:30 A.M. on Sept. 14, 1979 under 100 foot-candle light intensity at Salinas, Calif. are denoted by (b).

Classification:

*Botanical.*—*Dianthus caryophyllus,* L. Queen.

*Commercial.*—Spray carnation for cut flower production.

Inflorescence characteristics:

*Flowering response.*—Medium, ranging from 22 weeks (at Salinas, Calif. grown pinched from a July 5 plant date) to 30 weeks (at Barberton, Ohio grown pinched from an October 22 plant date).

*Inflorescence type.*—Semi-compound spray, with 1 to 4 buds per lateral, with reduced bud count during lower light periods; occasionally seen as a terminal spray, with 1 bud per lateral, especially on second cropping.

*Number of buds and flowers per stem.*—4 to 7 showing color on first crop.

*Peduncle length.*—Medium, ranging from 10 to 12 cm. on top flower.

*Peduncle strength.*—Strong, holding flowers erect in all periods; shows tendency toward brittleness during low light periods.

*Flower.*—Size: Medium, 45 to 65 mm. in diameter when grown as a spray; too small for adaption as a commercial disbud. Type: Commercial double, petals from 20 to 25 in number. Form: Flat, twisting slightly with maturity.

*Corolla.*—Smooth texture, both abaxial and adaxial; deeply serrated petal margin.

*Corolla color.*—General tonality from a distance of 3 meters: Light salmon pink, approximately 38-2 to 38-1 (a,b). Abaxial: Approximately 36-2 oxidizing to 36-1 (a), to 39-2 oxidizing to 39-1 (b). Adaxial: 36-1 (a) to 39-1 (b).

*Keeping quality.*—On plant, up to 18 days; as a cut flower up to 15 days under room temperature of 20° C.

*Fragrance.*—Very slight to none, typical carnation.

*Reproductive organs.*—Androecium: Typical carnation, normal in all respects; long filament length, moderate to abundant pollen. Gynoecium: Typical carnation, normal in all respects; white pistil of medium length, approximately 30 to 32 mm.

Plant characteristics:

*Growth and duration.*—Bushy and vigorous semi-erect perennial; typical of cultivars adaptable to commercial cut spray production; similar to that of Silvery Pink.

*Branching pattern.*—Semi-erect, numerous and unrestricted at base of plant.

*Height.*—Tall, 80 to 85 cm. at time of first cut grown as a pinched plant.

*Stem.*—Strong, with bend of 5 to 10 degrees (Society of American Florist's Standards), almost brittle during low light periods; approximately 50 to 55 cm. in length from top to first vegetative lateral.

*Foliage.*—Occurrence: Abundant; typical carnation; similar to that of Silvery Pink. Color (Abaxial): Approximately 21-14 to 21-15 but more greyed (a,b). Color (Adaxial): Approximately 21-14 but more greyed (a,b).

CHART A.

COMPARISON OF QUEEN, SWEETHEART, AND SILVERY PINK

| CULTIVAR | FLOWER COLOR | FLOWER SIZE | NO. OF BUDS & FLOWERS PER STEM | FLOWERING RESPONSE PERIOD |
|---|---|---|---|---|
| QUEEN | light salmon pink | 45 to 60 mm | 4 to 7 | 22 to 30 weeks |
| SWEETHEART | light salmon pink | 50 to 70 mm | 3.5 to 6 | 27 to 30 weeks |
| SIVLERY PINK | light lavender pink | 55 to 75 mm | 4 to 7 | 25 to 39 weeks |

| CULTIVAR | PEDUNCLE LENGTH | PEDUNCLE STRENGTH | PENDUNCLE HEIGHT |
|---|---|---|---|
| QUEEN | medium, 10 to 12 cm | strong | tall, 80 to 85 cm |
| SWEETHEART | medium, 9 to 11 cm | medium | short, 65 to 75 cm |
| SIVLERY PINK | long, 12 to 14 cm | weak | tall, 75 to 80 cm |

COMPARISON MADE OF PINCHED, FLOWERING PLANT GROWN IN BARBERTON, OHIO AND SALINAS, CALIFORNIA

We claim:

1. A new and distinct cultivar of *Dianthus caryophyllus,* L. known by the cultivar name Queen, as described and illustrated, and particularly characterized as to uniqueness by the combined characteristics of commercial double flower type; flat flower form, twisting slightly with maturity; medium flower size, light salmon pink flower color with minimum color oxidation; medium flowering response; 4 to 7 flowers and buds showing color per flowering stem; medium peduncle length; strong peduncle strength; and tall plant height.

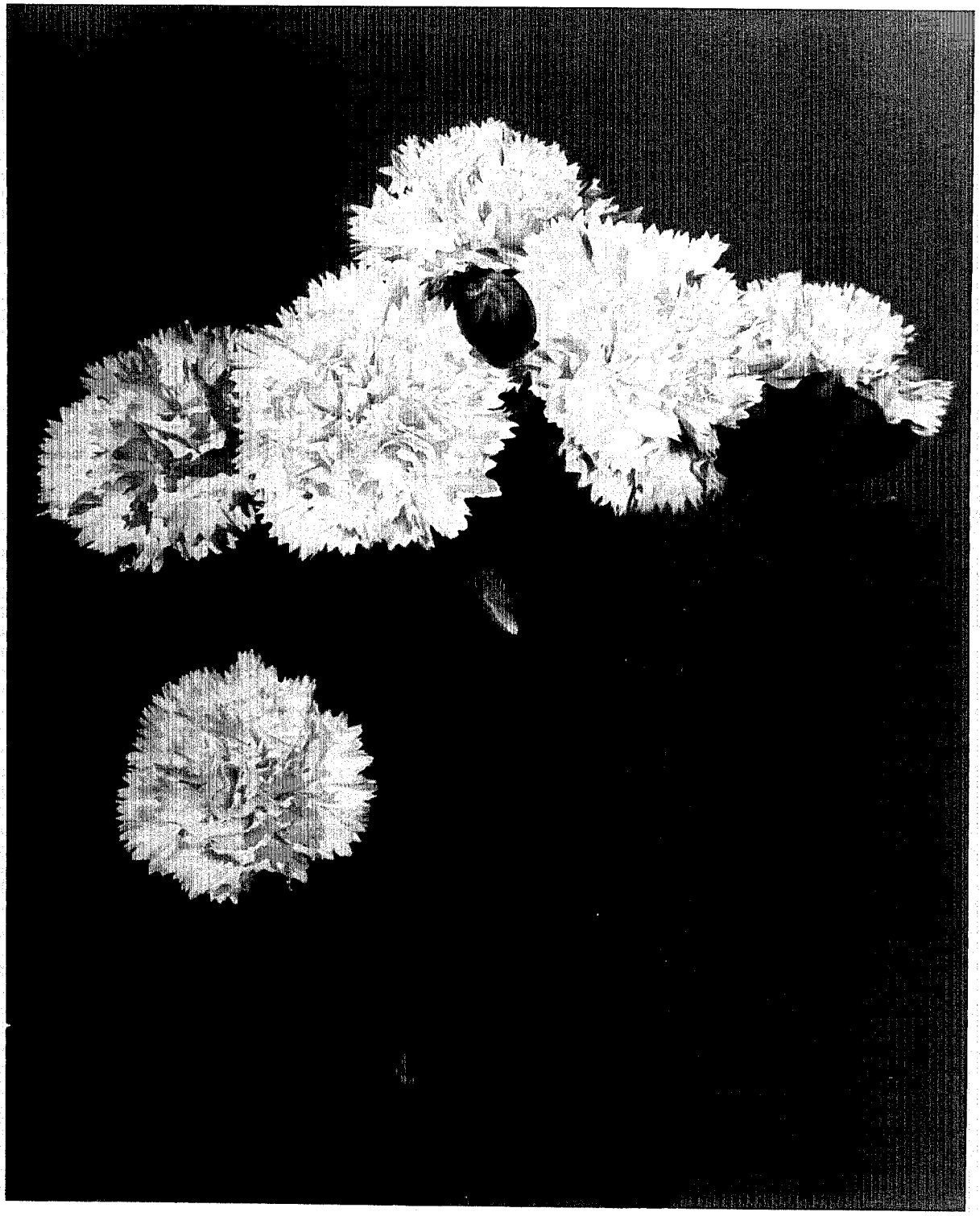

* * * * *